United States Patent
Bourissou et al.

(10) Patent No.: US 8,563,679 B2
(45) Date of Patent: Oct. 22, 2013

(54) CATALYTIC SYSTEMS FOR THE RING-OPENING (CO)POLYMERIZATION OF LACTONES

(75) Inventors: Didier Bourissou, Plaisance du Touch (FR); Blanca Martin-Vaca, Toulouse (FR); Aurelie Alba, Auch (FR); Roland Cherif-Cheikh, Castelldefels (ES); Anne-Paula De Sousa Delgado, Molins de Rei (ES)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 187 days.

(21) Appl. No.: 12/990,610

(22) PCT Filed: Apr. 29, 2009

(86) PCT No.: PCT/FR2009/000503
§ 371 (c)(1),
(2), (4) Date: Nov. 1, 2010

(87) PCT Pub. No.: WO2009/138589
PCT Pub. Date: Nov. 19, 2009

(65) Prior Publication Data
US 2011/0054144 A1 Mar. 3, 2011

(30) Foreign Application Priority Data
Apr. 30, 2008 (FR) .................... 08 02437

(51) Int. Cl.
*C08G 63/82* (2006.01)
(52) U.S. Cl.
USPC ........... 528/356; 528/330; 528/332; 528/346; 528/354; 564/83

(58) Field of Classification Search
USPC ................. 528/330, 332, 346, 356; 564/83
See application file for complete search history.

(56) References Cited

U.S. PATENT DOCUMENTS

| 3,655,631 A | 4/1972 | Fraser et al. |
| 2005/0004338 A1* | 1/2005 | Smith et al. ............... 528/89 |

FOREIGN PATENT DOCUMENTS

| JP | 2006/225586 | 8/2006 |
| JP | 2007/023271 | 2/2007 |
| WO | 2004/052980 | 6/2004 |

OTHER PUBLICATIONS

Wu et al Synthesis, characterization of aluminum complexes and the application in ring opening polymerization of l-lactide, European polymer journal, 43 (2007), 5040-5046, published Jul. 17, 2007.*
Zhao et al Synthesis and reactions of aluminum sulfonamide alkyls and hydride, Organometallics, 207, 26,1947-1954, published Mar. 15, 2007.*
Eagle, Cassandra T. et al., Journal of Chemical Crystallography, vol. 32, No. 7, pp. 165-170, Jul. 2002 XP-002504641.
Hormnirun, et al. (2004) *J. Am. Chem. Soc.* 126: 2688-2689.
Kondo, el al. (2005) *Bull. Chem. Soc. Jpn.* 78: 1348-1350.
Nomura, et al. (2002) *J. Am. Chem. Soc.* 124: 5938-5939.

* cited by examiner

*Primary Examiner* — Gregory Listvoyb
(74) *Attorney, Agent, or Firm* — Hunton & Williams LLP

(57) ABSTRACT

The present invention relates to the use of a system composed of a base and of a sulphonamide, as a catalyst for the ring-opening (co)polymerization of lactones. The present invention also relates to novel sulphonamides and to a process for the ring-opening (co)polymerization of lactones comprising the use of sulphonamides in combination with a base as a catalytic system.

20 Claims, No Drawings

CATALYTIC SYSTEMS FOR THE RING-OPENING (CO)POLYMERIZATION OF LACTONES

This application is a national stage of filing of PCT/FR2009/000503, filed Apr. 29, 2009, the subject matter of which is incorporated herein in its entirety. This application further claims priority to FR 0802437 filed Apr. 30, 2008, the subject matter of which is incorporated herein in its entirety.

FIELD OF INVENTION

The present invention relates to the use of a system constituted by a base and a sulphonamide, as a catalyst for the ring-opening (co)polymerization of lactones. The present invention also relates to novel sulphonamides and a process for the ring-opening (co)polymerization of lactones comprising the use of sulphonamides in combination with a base as a catalytic system.

BACKGROUND OF INVENTION

Nowadays, increasing attention is paid to synthetic polymers for the development of artificial organs and the formulation of medicaments [*Chem. Eng. News* 2001, 79 (6), 30]. The polymers concerned must satisfy a certain number of criteria and, in particular, they must be biocompatible. Biodegradable character is an additional advantage if the polymer must be eliminated after an appropriate period of implantation in an organism. In this respect, copolymers based on lactic and glycolic acid (PLGA) are of great interest as they are susceptible to hydrolysis and are degraded in vivo with the release of non-toxic by-products. The field of application of PLGAs is very wide (*Adv. Mater.* 1996, 8, 305 and *Chemosphere* 2001, 43, 49). In the surgical field, they are used for the synthesis of multi-strand wires, sutures, implants, prostheses etc. In pharmacology, they allow the encapsulation, transfer and controlled release of active ingredients.

For all these applications, the key factor is the degradation rate of the PLGAs which of course depends on their structure (chain length, dispersity, proportion, stereochemistry and chain formation of the monomers etc.). In the last few years, numerous works have therefore been devoted to the development of catalysts and/or primers of (co)polymerization, i.e. lactide and/or glycolide polymerization or copolymerization, making it possible to prepare PLGAs with a controlled structure.

The use of metallic systems most often leads to a contamination of the copolymers thus obtained by the presence of metal salts, which sometimes constitutes a significant limitation depending on the applications envisaged. The development of non-metallic systems allowing the controlled (co)polymerization of lactide and/or glycolide therefore constitutes a major challenge. The present invention comes within this context.

The Applicant therefore proposes the use of a simple catalytic system, constituted by a (co)polymerization catalyst and additive, and which makes it possible to control the chain length but also the nature of the chain ends of the prepared (co)polymers.

DETAILED DESCRIPTION OF THE INVENTION

A subject of the present invention is therefore the use of a sulphonamide in combination with a base as a catalytic system for the ring-opening (co)polymerization of lactones.

The term (co)polymerization means polymerization or copolymerization. This term includes the term (co)oligomerization, which means oligomerization or cooligomerization with degrees of polymerization (DP) less than 30. Thus, for example, lactide and glycolide (co)polymerization covers lactide polymerization, glycolide polymerization but also lactide and glycolide copolymerization. The term (co)polymer means polymer or copolymer. This term includes the term (co)oligomer, which means oligomer or cooligomer with degrees of polymerization (DP) less than 30. Thus, for example, a lactide and glycolide (co)polymer covers a lactide polymer, a glycolide polymer but also a lactide and glycolide copolymer.

According to the present invention, the term sulphonamide represents a molecule comprising at least one —$SO_2$—NH— function, such as a monosulphonamide or a bisulphonamide. The term monosulphonamide represents a molecule comprising an —$SO_2$—NH— function, and the term bisulphonamide represents a molecule comprising two —$SO_2$—NH— functions.

A more particular subject of the invention is the use of a sulphonamide as defined above for the (co)polymerization of dilactones.

A subject of the invention is also the use of a sulphonamide as defined above for lactide and/or glycolide copolymerization, and preferentially for lactide polymerization.

According to the present invention, the base used is preferentially a tertiary amine;
and more particularly, a tertiary amine chosen from:
  diisopropylethylamine;
  sparteine;
  N,N-dimethylcyclohexylamine;
  N,N,N"N"-tetramethyl-1,2-cyclohexanediamine; and
  4-dimethylaminopyridine.

According to a variant of the invention, the sulphonamide used is a monosulphonamide, and preferably a mono sulphonamide of general formula (I):

(I)

in racemic, or enantiomeric form or any combination of these forms, in which:

R1 and R2 represent independently an alkyl, haloalkyl or aryl radical, optionally substituted.

Within the meaning of the present invention, the aryl radicals can be of mono- or polycyclic aromatic type. The monocyclic aryl radicals can be chosen from the phenyl, tolyl, xylyl, mesityl, cumenyl and preferably phenyl radicals. The polycyclic aryl radicals can be chosen from the naphthyl, anthryl, phenanthryl, fluorenyl radicals. They can be optionally substituted by one or more radicals such as alkyl, haloalkyl, alkoxy, alkoxycarbonyl, alkylcarbonyloxy, halo, cyano, nitro, aryl, aryloxy, aryloxycarbonyl, arylcarbonyloxy.

The expression halo means fluoro, chloro, bromo or iodo, and preferably fluoro.

The expression alkyl represents an alkyl radical with 1 to 8 carbon atoms. This expression covers the linear or branched alkyl radicals having 1 to 6 carbon atoms and in particular the alkyl radicals having 1 to 4 carbon atoms such as the methyl, ethyl, propyl, isopropyl, butyl, isobutyl, sec butyl and tert butyl radicals, and preferably methyl. The expression also covers the radicals comprising more than 6 carbon atoms such as the heptyl and octyl radicals.

The term haloalkyl represents an alkyl radical as defined above substituted by one or more identical or different halo groups as defined above, such as for example trifluoromethyl, 1,2-dichloroethyl and preferably trifluoromethyl.

The term aryloxy denotes the radicals in which the aryl radical is as defined above such as for example the phenyloxy, tolyloxy, naphthyloxy, anthryloxy and phenanthryloxy radicals. The term aryloxycarbonyl preferably denotes the radicals in which the aryloxy radical is as defined above, such as for example phenyloxycarbonyl, tolyloxycarbonyl.

The term arylcarbonyloxy preferably denotes the radicals in which the aryl radical is as defined above, such as for example phenylcarbonyloxy, tolylcarbonyloxy or naphthyl carbonyl oxy.

The term alkoxy denotes the radicals in which the alkyl radical is a radical with 1 to 8 carbon atoms as defined above such as for example the methoxy, ethoxy, propyloxy or isopropyloxy but also linear, secondary or tertiary butoxy, pentyloxy radicals.

The term alkoxycarbonyl preferably denotes the radicals of alkyl-O—C(O)-type in which the alkyl radical is as defined above such as for example methoxycarbonyl, ethoxycarbonyl.

The term alkylcarbonyloxy preferably denotes the radicals of alkyl-C(O)—O-type in which the alkyl radical is as defined above such as for example methylcarbonyloxy, ethylcarbonyloxy.

A subject of the invention is also preferably the use of a monosulphonamide of general formula (I), in which R1 and R2 represent independently a phenyl, alkyl or haloalkyl radical.

A more particular subject of the invention is the use of a sulphonamide as defined above chosen from:

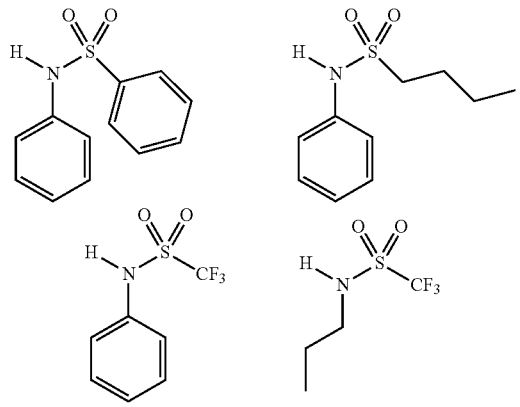

According to another variant of the invention, the sulphonamide used is a bisulphonamide, and preferably a bisulphonamide of general formula (IIa) or (IIb)

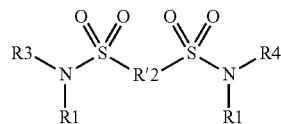

(IIa)

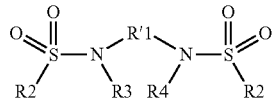

(IIb)

in racemic, or enantiomeric form or any combination of these forms, in which:

R1 and R2 represent an alkyl, haloalkyl or aryl radical, optionally substituted;

R'1 and R'2 represent an arylene, alkylene, cycloalkylene radical, all these radicals being optionally substituted;

R3 and R4 represent independently a hydrogen atom or an alkyl radical, preferentially R3 and R4 represent independently a hydrogen atom or a methyl radical and very preferentially R3 and R4 represent a hydrogen atom.

Within the meaning of the present invention, the term arylene represents a divalent aryl group, the aryl group being as defined previously, the term alkylene represents a divalent alkyl group, the alkyl group being as defined previously and the term cycloalkylene denotes a divalent cycloalkyl group, the cycloalkyl group being as defined below.

The cycloalkyl radicals are chosen from the saturated or unsaturated monocyclic cycloalkyls. The saturated monocyclic cycloalkyl radicals can be chosen from the radicals having 3 to 7 carbon atoms such as the cyclopropyl, cyclobutyl, cyclopentyl, cyclohexyl or cycloheptyl radicals. The unsaturated cycloalkyl radicals can be chosen from the cyclobutene, cyclopentene, cyclohexene, cyclopentadiene, cyclohexadiene radicals.

Very preferentially, R1 and R2 represent an optionally substituted phenyl, alkyl or haloalkyl radical; R1 represents an cycloalkylene, alkylene radical optionally substituted by a phenyl radical; R'2 represents an alkylene or phenylene radical.

More particularly, R1 and R2 represent an alkyl, trifluoromethyl radical or a phenyl radical optionally substituted by methyl or trifluoromethyl.

A more particular subject of the invention is the use of a sulphonamide chosen from:

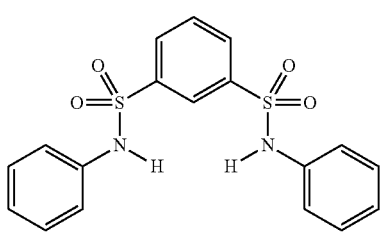

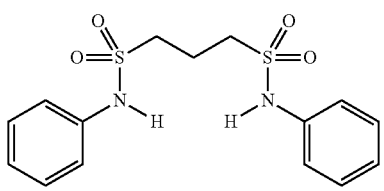

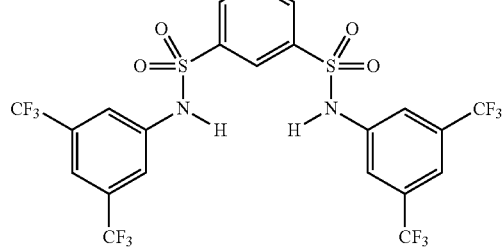
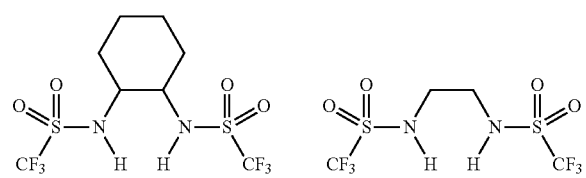
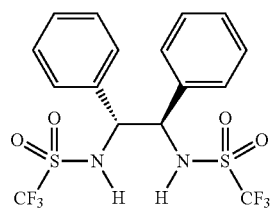
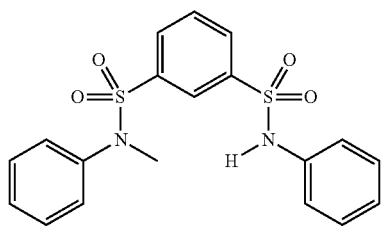
and even more particularly chosen from:
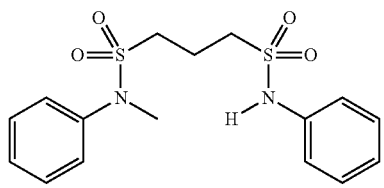
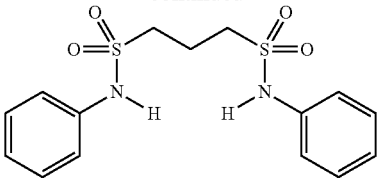
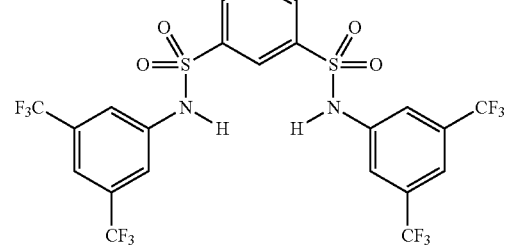
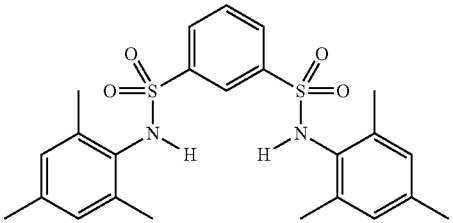
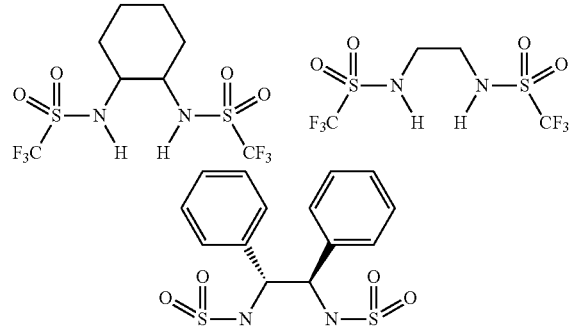
Very preferentially, the base used for the present invention is 4-dimethylaminopyridine.
A subject of the invention is also the following compounds:
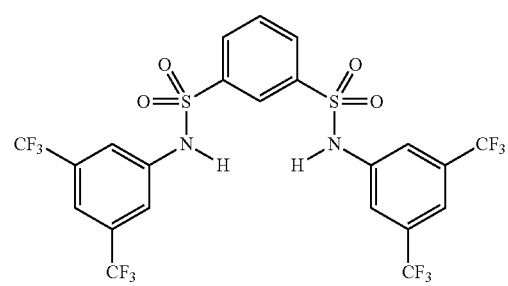
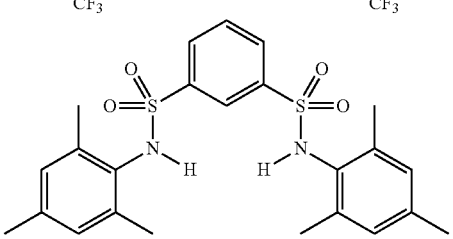

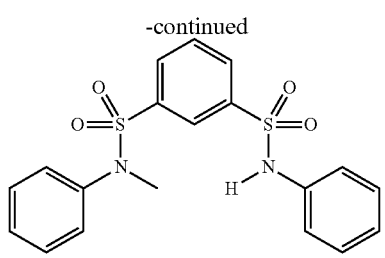

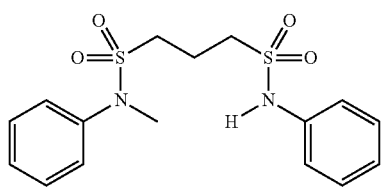

as sulphonamides as defined above, and more preferentially, a subject of the invention is also the following compounds:

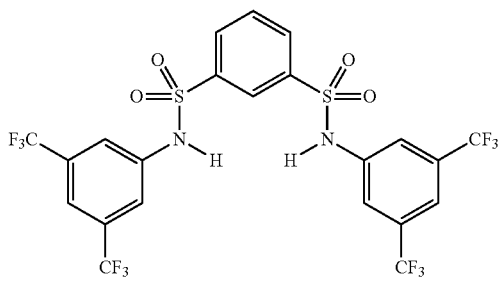

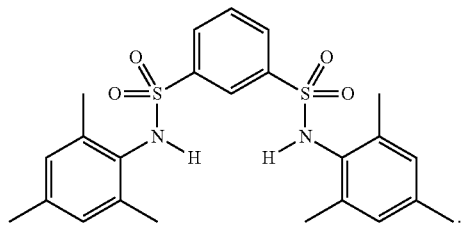

A more particular subject of the invention is also a process for the ring-opening (co)polymerization characterized in that it involves the use of a sulphonamide in combination with a base as a catalyst, as defined previously.

Preferentially, this process uses a (co)polymerization solvent, at a temperature comprised between 0° C. and 250° C. (more preferentially between ambient temperature and 150° C.), for a duration comprised between a few minutes and 300 hours (more preferentially between one hour and 72 hours). The temperature is chosen as a function of the solvent such that it is within the above range and at most the boiling temperature of the solvent if this temperature is below 250° C.

Very preferentially, this process involves lactide and/or glycolide as monomer.

The present invention has numerous advantages, in particular:
the catalytic systems are easily accessible and inexpensive;
the sulphonamides are synthesized simply and with good yields;
the sulphonamides have various structures, making it possible to envisage numerous different catalytic systems;
the sulphonamides have structures which are stable in air at ambient temperature;
the mass distribution of the polymers obtained is very narrow; the polydispersity indices obtained by means of the present invention are in fact comprised between 1.05 and 1.20;
the ring-opening (co)polymerization catalyzed by the sulphonamides is reproducible;
the ring-opening (co)polymerization catalyzed by the sulphonamides can be implemented in various solvents such as dichloromethane, toluene or tetrahydrofuran.

The invention finally relates to lactide and/or glycolide polymers or copolymers obtained or capable of being obtained by the implementation of a process as described above.

Unless defined otherwise, all the technical and scientific terms used in the present Application have the same meaning as that usually understood by an ordinary specialist in the field to which the invention belongs.

The catalysts prepared all comprise one or two —$SO_2NH$— functions: the terms monosulphonamide and bisulphonamide respectively are then used.

The following experimental part is presented in order to illustrate the above procedures and should in no event be considered as limiting the scope of the invention.

EXPERIMENTAL PART

The products were characterized according to the standard methods known to a person skilled in the art described below.

The $^1H$, $^{13}C$, and $^{19}F$ NMR spectra are obtained on Bruker Avance 300 spectrometers. The shifts are counted positively towards the strong fields, and expressed in ppm. The references are tetramethylsilane for $^1H$ and $^{13}C$, and trifluoroacetic acid for $^{19}F$. The following abbreviations were used to describe the signals: s (singlet), br s (broad singlet), d (doublet), t (triplet), q (quadruplet), qt (quintuplet), dd (doublet of doublets), m (multiplet).

The melting points were measured on an Electrothermal digital instrument.

The mass spectra were produced using the chemical ionization (CI) or electron impact (EI) methods on Thermo TSQ 700, Applied Biosystem API-365 or Applied Biosystem Qtrap spectrometers. High resolution analyses (HRMS) were carried out on a Waters Micromass LCT instrument.

The number average (Mn) and weight average (Mw) molecular masses of the polymers, as well as the polydispersity indices (PI), are determined by steric exclusion chromatography on an HPLC Waters 712 system (in THF, 1 mL/min, T=35° C., Styragel HR1 or Styragel HR4E column, calibration with polystyrene standards).

Preparation 1: Preparation of the Sulphonamides From Sulphonyl Chloride (Examples 1 to 6)

A first family is obtained from a backbone comprising one or two sulphonyl chloride functions, onto which the chosen amine is grafted. These catalysts, which are stable in air and at ambient temperature, have been fully characterized ($^1H$, $^{13}C$ NMR, MS, elementary analyses, melting point).

Preparation 1a: Preparation of Monosulphonamides

The monosulphonamides were prepared as follows:

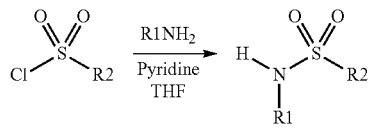

Sulphonyl chloride R2SO$_2$Cl (1 equivalent) is slowly added to a mixture of amine R1NH$_2$ (1 equivalent) and pyridine (1 equivalent) in tetrahydrofuran (1.8 mol·L$^{-1}$) and the reaction medium is stirred at ambient temperature, i.e. at a temperature comprised between 18° C. and 30° C., until total conversion of the reagents is achieved, the progress of the reaction being monitored by $^1$H NMR. The solvent is then evaporated off under vacuum and the crude product obtained is purified by chromatography on a silica column, the mobile phase being a CH$_2$Cl$_2$/MeOH gradient.

The following monosulphonamides were thus prepared:

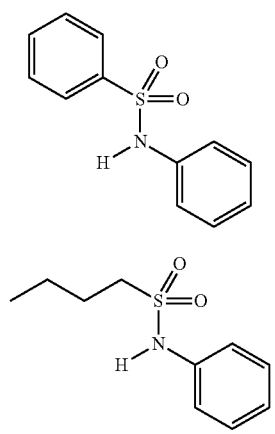

Example 1

NMR $^1$H (CDCl$_3$, 300 MHz): δ 7.03 (s, 1H, NH); 7.23-7.31 (m, 3H, CH); 7.39-7.43 (m, 2H, CH); 7.58-7.63 (m, 2H, CH); 7.68-7.73 (m, 1H, CH); 7.96 (d, $^3$J=7.7 Hz, 2H, CH) ppm; $^{13}$C (CDCl$_3$, 75 MHz): δ 121.7 (CH); 125.5 (CH); 127.3 (CH); 129.1(CH); 129.4 (CH); 133.1 (CH); 136.4 (C), 138.96 (C) ppm; MS (EI): 233 [M]$^{+}$; Elementary analysis: Calculated for (C$_{12}$H$_{11}$NO$_2$S) C 61.78%, H 4.75%, N 6.00%. Measured C 61.86%, H 4.50%, N 5.97%. Melting point: 110.5-112.0° C.

Example 2

NMR $^1$H (CDCl$_3$, 300 MHz): δ 0.90 (t, $^3$J=7.2 Hz, 3H, CH$_3$); 1.36-1.48 (m, 2H, CH$_2$); 1.75-1.86 (m, 2H, CH$_2$); 3.06-3.12 (m, 2H, CH$_2$); 6.31 (s, 1H, NH); 7.15-7.21 (m, 3H, CH); 7.32-7.38 (m, 2H, CH) ppm; $^{13}$C (CDCl$_3$, 75 MHz): δ 13.4 (CH$_3$); 21.3 (CH$_2$); 25.2 (CH$_2$); 51.1 (CH$_2$); 120.3 (CH); 124.8 (CH); 129.5 (CH); 137.1 (C) ppm; MS (EI): 213 [M]$^{+}$; Elementary analysis: Calculated for (C$_{10}$H$_{15}$NO$_2$S) C 56.31%, H 7.09%, N 6.57%. Measured C 55.72%, H 7.27%, N 6.42%.

Preparation 1b: Preparation of Bisulphonamides

The bisulphonamides were prepared according to the following procedure:

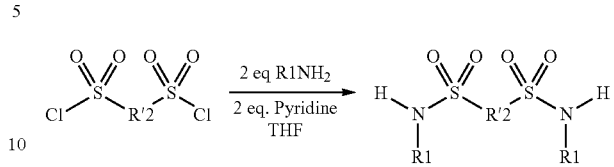

Sulphonyl chloride (1 equivalent) is added to a mixture of amine R1NH$_2$ (2 equivalents) and pyridine (2 equivalents) in tetrahydrofuran (1 mol·L$^{-1}$). The reaction medium is stirred at ambient temperature until total conversion of the reagents is achieved, the progress of the reaction being monitored by $^1$H NMR. The solvent is then evaporated off under vacuum and the crude product obtained is purified by chromatography on a silica column, the mobile phase being a CH$_2$Cl$_2$/MeOH gradient.

The following bisulphonamides were thus prepared:

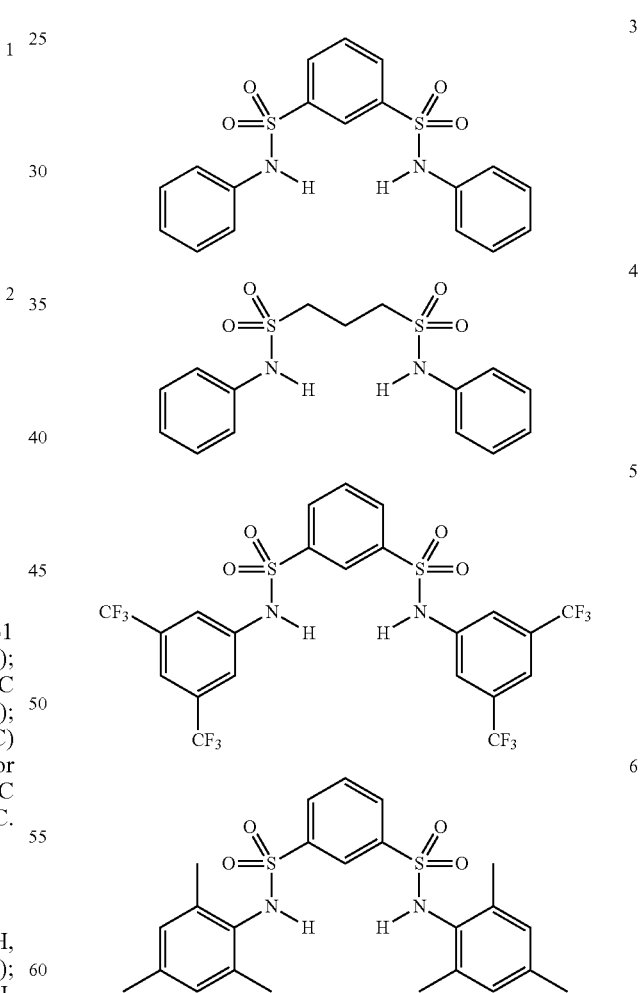

Example 3

NMR $^1$H (CD$_3$OD, 300 MHz): δ 6.97-7.21 (m, 10H, CH); 7.55 (t, $^3$J=7.8 Hz, 1H, CH); 7.86 (dd, 2H, $^4$J=1.5 Hz and $^3J=7.8$ Hz, 2H, CH); 8.16 (t, $^4J=1.5$ Hz, 1H, CH) ppm; $^{13}$C (CD$_3$OD, 75 MHz): δ 122.6 (CH); 126.2 (CH); 127.0 (CH); 130.3 (CH); 131.0 (CH); 132.0 (CH); 138.3 (C); 142.3 (C) ppm; MS (EI): 388 [M]$^+$; Elementary analysis: Calculated for (C$_{18}$H$_{14}$N$_2$O$_4$S$_2$) C 55.65%, H 5.15%, N 7.21%. Measured C 56.13%, H 3.82%, N 7.21%; Melting point: 157° C.

Example 4

NMR $^1$H (CDCl$_3$, 300 MHz): δ 2.36-2.41 (qt, $^3J=7.2$ Hz, 2H, CH$_2$); 3.27-3.32 (t, $^3J=7.2$ Hz, 4H CH$_2$); 7.04 (s, 2H, NH); 7.18-7.23 (m, 4H, CH); 7.27 (m, 2H, CH); 7.35 (m, 4H, CH) ppm; $^{13}$C (CDCl$_3$, 75 MHz): δ 18.1 (CH$_2$); 48.8 (CH$_2$); 121.2 (CH); 125.7 (CH); 129.8 (CH); 136.4 (C) ppm; MS (EI): 354 [M]$^+$; Elementary analysis: Calculated for (C$_{15}$H$_{18}$N$_2$O$_4$S$_2$) C 50.83%, H 5.12%, N 7.90%. Measured C 51.01%, H 4.74%, N 7.85%. Melting point: 129.8-131.6° C.

Example 5

NMR $^1$H (CD$_3$OD, 300 MHz): δ 7.58 (s, 4H, CH); 7.60 (s, 2H, CH); 7.74 (t, 1H, $^3J=1.7$ Hz, CH); 8.03 (dd, $^4J=1.7$ Hz, $^3J=7.7$ Hz, 2H, CH); 8.21 (t, $^3J=7.7$ Hz, 1H, CH) ppm; $^{13}$C (CD$_3$OD, 75 MHz): δ 118.7 (q, J$_{CF}$=3.9 Hz, CH); 120.9 (q, J$_{CF}$=3.5 Hz, CH); 124.2 (q, J$_{CF}$=271.6 Hz, CF$_3$); 126.6 (C); 132.1 (CH); 132.5 (CH); 133.9 (q, J$_{CF}$=33.7 Hz, C); 140.6 (C); 142.2 (C) ppm; $^{19}$F (CD$_3$OD, 280 MHz): δ −63.2 ppm; MS (CI): 678 [M+NH$_4$]$^+$; Elementary analysis: Calculated for (C$_{22}$H$_{12}$F$_{12}$N$_2$O$_4$S$_2$) C 40.01%, H 1.83%, N 4.24%. Measured C 40.38%, H 1.26%, N 4.19%; Melting point: 159.0-159.6° C.

Example 6

NMR $^1$H (CDCl$_3$, 300 MHz): δ 2.00 (s, 12H, CH$_3$); 2.25 (s, 6H, CH$_3$); 6.71 (s, 2H, NH); 6.84 (s, 4H, CH); 7.51 (t, $^3J=7.8$ Hz, 1H, CH); 7.80-7.83 (q, $^4J=1.7$ Hz, $^3J=7.8$ Hz, 2H, CH); 8.58 (t, $^4J=1.7$ Hz, 1H, CH) ppm; $^{13}$C (CDCl$_3$, 75 MHz): δ 18.7 (CH$_3$); 20.9 (CH$_3$); 125.8 (CH); 129.3 (C); 129.7 (CH); 130.0 (CH); 131.1 (CH); 137.5 (C); 138.1 (C); 142.6 (C) ppm; MS (EI): 233 [M]$^+$; Elementary analysis: Calculated for (C$_{24}$H$_{28}$N$_2$O$_4$S$_2$) C 60.99%, H 5.97%, N 5.93%. Measured C 60.90%, H 5.91%, N 5.85%. Melting point: 197.9-199.5° C.

Preparation 2: Preparation of the Sulphonamides From Sulphonic Anhydride (Examples 7 to 11)

A second family of sulphonamides was also synthesized from the amines, by reaction with trifluoromethanesulphonic anhydride.

The catalysts thus prepared were characterized. They are stable in air and at ambient temperature.

Preparation 2a: Preparation of Monosulphonamides

The monosulphonamides were prepared according to the following procedure:

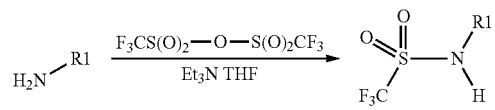

A solution of trifluoromethanesulphonic anhydride (1.1 equivalents, 3 mol·L$^{-1}$) in anhydrous dichloromethane is slowly added to a mixture of amine (1 equivalent, 3 mol·L$^{-1}$) and triethylamine (1.1 equivalents) in anhydrous dichloromethane at 0° C. The reaction medium is stirred for an hour at 0° C., then, after returning to ambient temperature, a saturated aqueous solution of NaCl is added. The aqueous phase is extracted twice with dichloromethane. The organic phases are combined, dried over anhydrous sodium sulphate, filtered and concentrated to dryness. The crude residue obtained is purified by chromatography on a silica column, the mobile phase being a CH$_2$Cl$_2$/MeOH gradient.

The following monosulphonamides were prepared:

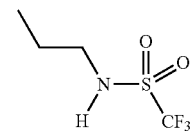

7

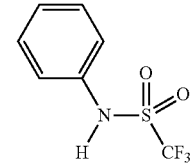

8

Example 7

NMR $^1$H (CDCl$_3$, 300 MHz): δ 0.95-1.00 (t, $^3J=7.1$ Hz, 3H, CH$_3$); 1.58-1.70 (m, 2H, CH$_2$); 3.25-3.30 (t, $^3J=7.4$ Hz, 2H, CH$_2$); 4.89 (br s, 1H, NH) ppm; $^{19}$F (CDCl$_3$, 280 MHz): δ −77.4 ppm; MS (EI): 191 [M]$^+$, 162 [M−C$_2$H$_5$]$^+$.

Example 8

NMR $^1$H (CDCl$_3$, 300 MHz): δ 7.19-7.28 (m, 3H, CH); 7.31-7.36 (m, 2H, CH); 6.63 (br s, 1H, NH) ppm; $^{19}$F (CDCl$_3$, 280 MHz): δ −75.2 ppm; MS (EI): 225 [M]$^+$.

Preparation 2b: Preparation of Bisulphonamides

The bisulphonamides were prepared according to the following procedure:

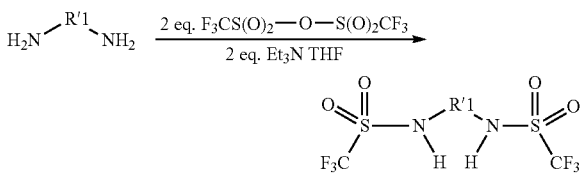

A solution of trifluoromethanesulphonic anhydride (2.1 equivalents, 5 mol·L$^{-1}$) in anhydrous dichloromethane is slowly added to a mixture of diamine (1 equivalent, 3 mol·L$^{-1}$) and triethylamine (2.1 equivalents) in anhydrous dichloromethane at 0° C. The reaction medium is stirred cold for one hour, then after returning to ambient temperature, a saturated solution of NaCl is added. The aqueous phase is extracted twice with dichloromethane. The organic phases are combined, dried over anhydrous sodium sulphate, filtered and concentrated to dryness. The crude residue obtained is purified by chromatography on a silica column, the mobile phase being a CH$_2$Cl$_2$/MeOH gradient.

The following bisulphonamides were prepared:

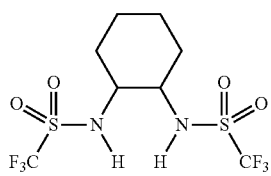

9

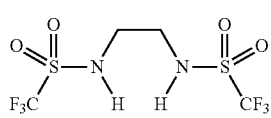

10

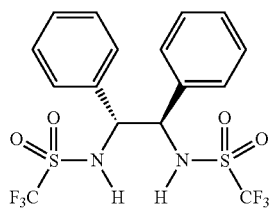

11

Example 9

NMR $^1$H ((CD$_3$)$_2$CO), 300 MHz): δ 1.37-1.41 (m, 2H, CH); 1.67-1.71 (m, 2H, CH); 1.77-1.81 (m, 2H, CH); 2.11-2.15 (m, 2H, CH); 3.34 (m, 2H, CH); 7.98 (br s, 2H, NH) ppm; $^{33}$C ((CD$_3$)$_2$CO), 75 MHz): δ 24.3 (CH$_2$); 33.2 (CH$_2$); 58.8 (CH); 115-128 (q, J$_{CF}$=320.5 Hz, CF$_3$); $^{19}$F ((CD$_3$)$_2$CO), 280 MHz): δ −77.5 ppm; MS (EI): 378 [M]$^+$, 245 [M—SO$_2$CF$_3$]$^{+;}$ Melting point: 184.5-185.5° C.

Example 10

NMR $^1$H (C$_6$D$_6$, 300 MHz): δ 2.28 (s, 4H, CH$_2$); 4.00 (br s, 2H, NH); $^{13}$C (C$_6$D$_6$, 75 MHz): δ 43.4 (CH$_2$); 117-122 (q, J$_{CF}$=321.5 Hz, CF$_3$); $^{19}$F (C$_6$D$_6$, 280 MHz): δ−77 ppm; MS (CI): 342 (M+NH$_4$); Elementary analysis: Calculated for (C$_4$H$_6$F$_6$N$_2$O$_4$S$_2$) C 14.8%, H 1.87%, N 8.64%. Measured C 14.6%, H 1.90%, N 8.5% 1$^{st}$ test and C 40.48%, 112.36%, N 5.83% 2$^{nd}$ test. Melting point: 115-116° C.

Example 11

NMR $^1$H (CDCl$_3$, 300 MHz): δ 4.79 (s, 2H, CH); 5.87 (br s, 2H, NH); 6.97-7.00 (m, 4H, CH); 7.27 (m, 6H, CH) ppm; $^{19}$F (CDCl$_3$, 280 MHz): δ−77.3 ppm; MS (EI): Elementary analysis: Calculated for (C$_{16}$H$_{14}$F$_6$N$_2$O$_4$S$_2$) C 40.34%, H 2.96%, N 5.88%. Measured C 40.43%, H 2.36%, N 5.82%; Melting point: 213-215° C.

Preparation 3: Preparation of alkylated bisulphonamides (Examples 12 to 13)

The alkylated bisulphonamides were prepared according to the following procedure A or B:

Protocol A:

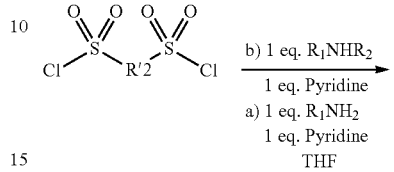

Protocol B:

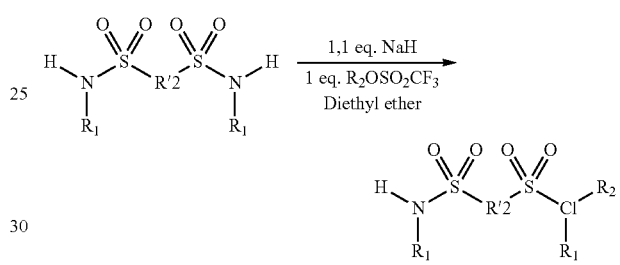

Example 12

One equivalent of 1,3-disulphonylbenzene chloride (5 g, 18 mmol) is introduced into one equivalent of pyridine (1.47 mL, 18 mmol) and one equivalent of N-methyl aniline (1.97 mL, 18 mmol) in solution in 50 ml of THF. After stirring for two hours at ambient temperature, one equivalent of aniline (1.66 mL, 18 mmol) and one equivalent of pyridine (1.47 mL, 18 mmol) are added. The mixture is stirred overnight at ambient temperature. The solvent is evaporated off under vacuum. The crude product obtained is dissolved in CH$_2$Cl$_2$, washed with a 0.1N HCl solution then with water, dried over sodium sulphate, filtered and evaporated. The solid obtained (nonmethylated/monomethylated/dimethylated mixture 0.33/1/0.33) is purified by chromatography on silica gel (eluent CH$_2$Cl$_2$/MeOH 95/5). The monomethylated sulphonamide 12 is obtained in the form of a white solid with a yield of 50%.

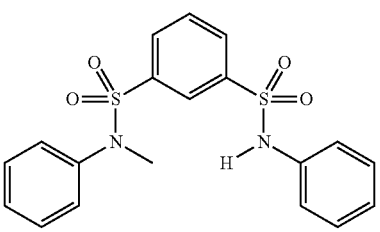

12

NMR $^1$H (CDCl$_3$, 300 MHz): δ 3.09 (s, 3H, CH$_3$); 6.84 (br s, 1H, NH); 6.94-6.98 (m, 2H, CH); 7.06 (m, 1H, CH); 7.09 (m, 1H, CH); 7.26-7.29 (m, 6H, CH); 7.49 (m, 1H, CH); 7.56-7.60 (m, 1H, CH); 7.91-7.94 (m, 1H, CH); 8.09 (t,

4J=1.5 Hz, 1H, CH) ppm; $^{13}$C (CDCl$_3$, 75.5 MHz): δ 38.4 (CH$_3$); 122.1 (CH); 126.2 (CH); 126.4 (CH); 126.6 (CH); 127.9 (CH); 129.2 (CH); 129.6 (CH); 129.7 (CH); 131.2 (CH); 131.9 (CH); 135.7 (C); 138.0 (C); 140.2 (C); 140.7 (C) ppm; HRMS DCI (CH$_4$): Calculated for 403.0786 (M+H+—C$_{19}$H$_{19}$N$_2$O$_4$S$_2$), Measured 403.0769 (−1.7; −4.2); Melting point: 162.0-162.6° C.

Example 13

Under an argon atmosphere, 1.1 equivalents of NaH (206 mg, 8.6 mmol, oil removed by three washings with pentane) are added to a solution of one equivalent of disulphonamide 4 (2.75 g, 7.8 mmol) in 100 mL of dried diethyl ether. After stirring for 30 minutes at ambient temperature, one equivalent of methyl triflate (880 µL, 7.8 mmol) is added. The reaction medium is stirred at ambient temperature overnight then the solvent is evaporated off. The crude product is re-dissolved in CH$_2$Cl$_2$, washed twice with a 1N HCl solution, then with a saturated salt solution, dried over sodium sulphate, filtered and re-evaporated. The solid obtained (nonmethylated/monomethylated/dimethylated mixture 0.4/0.2/0.4) is purified by chromatography on silica gel (eluent CH$_2$Cl$_2$/MeOH 95/5). Sulphonamide 13 is isolated in the form of a white powder with a yield of 12%.

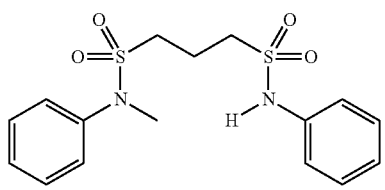

13

NMR $^1$H (CDCl$_3$, 300 MHz): δ 2.23 (m, 2H, CH$_2$); 3.13 (m, 4H, CH$_2$); 3.21 (s, 3H, CH$_3$); 7.08 (m, 1H, CH); 7.13-7.16 (m, 2H, CH); 7.19-7.24 (m, 3H, CH); 7.27 (m, 4H, CH); 7.34 (br s, 1H, NH) ppm; $^{13}$C (CDCl$_3$, 75.5 MHz): δ 18.0 (CH$_2$); 38.6 (CH$_3$); 47.1 (CH$_2$); 49.4 (CH$_2$); 120.8 (CH); 125.3 (CH); 126.7 (CH); 127.7 (CH); 129.5 (CH); 129.7 (CH); 136.6 (C); 140.9 (C) ppm; HRMS DCI (CH$_4$): Calculated for 369.0943 (M+H+—C$_{16}$H$_{21}$N$_2$O$_4$S$_2$), Measured 369.0957 (1.4; −3.8); Melting point: 93.6-94.2° C.

Preparation 4: Use of the Sulphonamide Catalysts in Ring-Opening Polymerization (ROP) of the Lactide The prepared catalysts were tested in ring-opening polymerization (ROP) of the D,L-lactide (or of the L-lactide) in combination with different bases: 4-dimethylaminopyridine (DMAP), sparteine, diisopropylethylamine (DIEA), N,N-dimethylcyclohexylamine (Me$_2$NCy), N,N,N"N"-tetramethyl-1,2-cyclohexanediamine ((Me$_2$N)$_2$Cy).

The lactide polymers were prepared according to the following procedure:

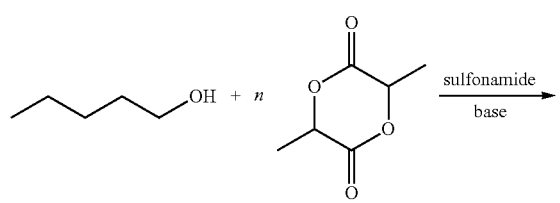

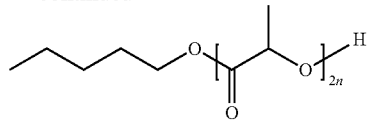

For all the polymerizations, the lactide, catalyst and base are dissolved in an anhydrous solvent (such as dichloromethane, toluene or tetrahydrofuran) in a Schlenk flask under argon. Pentanol is added and the reaction medium is stirred at ambient temperature. The conversion of the lactide to polymer is monitored by regularly taking a sample of solution which is concentrated, re-dissolved in CDCl$_3$, and checked by $^1$H NMR.

Example 14

The lactide (500 mg, 10 eq, 3.47 mmol), the catalyst of Example 3 (134 mg, 1 eq, 0.347 mmol) and DMAP (42 mg, 1 eq, 0.347 mmol) are dissolved in 3.5 mL of anhydrous dichloromethane in a Schlenk flask under argon. Pentanol (38 µL, 1 eq, 0.347 mmol) is added and the reaction medium is stirred at 26° C. The conversion of the lactide to polymer is monitored by regularly taking an aliquot of solution which is concentrated, re-dissolved in CDCl$_3$, and checked by $^1$H NMR.

A complete conversion Mn=1983 Mw=2217 PI=1.12

Various short-chain polymer syntheses made it possible to demonstrate the diversity of the sulphonamide/base pairs which can be used, all other experimental conditions otherwise being equal (CH$_2$Cl$_2$; molar ratio 5/1/1/1 of Lactide/Pentanol/Sulphonamide/Tertiary amine).

| Example | Sulphonamide | Base | Time | Conversion |
|---|---|---|---|---|
| 15 | 3 | DMAP | 5 h | 97% |
| 16 | 3 | Me$_2$NCy | 5 h | 77% |
| 17 | 3 | sparteine | 5 h | 73% |
| 18 | 7 | DIEA | 5 h 15 | 84% |
| 19 | 7 | sparteine | 5 h 15 | 91% |
| 20 | 7 | DMAP | 5 h | 94% |
| 21 | 7 | (Me$_2$N)$_2$Cy | 8 h | 80% |
| 22 | 9 (R, R) | Me$_2$NCy | 5 h | 98% |
| 23 | 10 | Me$_2$NCy | 6 h | 95% |
| 24 | 11 | Me$_2$NCy | 72 h | 64% |
| 25 | 5 | DMAP | 6 h | 84% |
| 26 | 6 | DMAP | 5 h 15 | 76% |

Polymers of different chain lengths can be synthesized in a controlled manner irrespective of the catalyst used.

Oligomers (molar ratios 5/1/1/1 of Lactide/Pentanol/Sulphonamide/DMAP or 10/1/1/1 in CH$_2$Cl$_2$) can thus be obtained in a rapid and controlled manner.

| Example | I/M | Catalyst | Time | Conversion | DP$_{NMR}$ |
|---|---|---|---|---|---|
| 27 | 5 | 3 | 3 h | 93% | 4.8 |
| 28 | 10 | 1 | 24 h | 93% | 9.9 |
| 29 | 10 | 2 | 40 h | 93% | 9.1 |
| 30 | 10 | 3 | 8 h | 88% | 8.7 |
| 21 | 10 | 4 | 8 h | 92% | 8.8 |
| 32 | 10 | 12 | 8 h | 67% | 5.8 |
| 33 | 10 | 13 | 7 h 30 | 55% | 5.2 |

I/M denotes the initial monomer/primer molar ratio used in the polymerization.

The DP$_{NMR}$ is the degree of polymerization of the polymer formed. It is determined by integration of the appropriate signals over the $^1$H NMR spectra.

It is also possible to synthesize larger polymers. The ratios used are then 50/1/10/10 (Lactide/Pentanol/Sulphonamide/DMAP) or 100/1/10/10. It is important to note the reproducible polydispersity indices of the polymers obtained:

| Example | I/M | Catalyst | Time | Conversion | Mn | Mw | PI |
|---|---|---|---|---|---|---|---|
| 34 | 10** | 3 | 8 h | 88% | 1765 | 2067 | 1.17 |
| 35 | 50** | 3 | 24 h | 90% | 7949 | 8413 | 1.06 |
| 36 | 50** | 5 | 24 h | 70% | 5296 | 5729 | 1.08 |
| 37 | 100* | 3 | 87 h 30 | 94% | 14830 | 16087 | 1.08 |
| 38 | 100** | 6 | 87 h 30 | 71% | 9540 | 10116 | 1.06 |

*L-lactide
**D,L-lactide

The synthesized polymers have masses corresponding to the monomer/primer ratio used, showing good control of the polymerization. The reaction times vary from 8 hours to three days, depending on the catalyst used and the degree of polymerization (DP) aimed at.

The above experimental results show that the sulphonamide catalysts allow lactide polymerization. Moreover the obtained polydispersity indices close to 1 show that these catalysts inhibit transesterifications.

The invention claimed is:

1. A method for ring-opening (co)polymerization of lactone(s) comprising copolymerization in the presence of a non-metallic catalytic system comprising a sulphonamide and a base, wherein said sulphonamide is a monosulphonamide of formula (I):

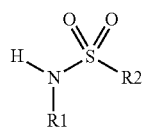

(I)

in racemic, or enantiomeric form or any combination thereof, wherein R1 and R2 represent independently an alkyl, halo alkyl, phenyl, haloalkyl radical, or aryl radical, wherein said aryl radical is optionally substituted or wherein the sulphonamide is a bisulphonamide of formula (IIa) or (IIb)

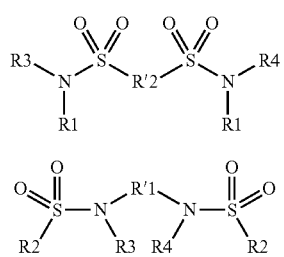

(IIa)

(IIb)

in racemic, or enantiomeric form or any combination thereof,
wherein R1 and R2 represent an alkyl, haloalkyl or aryl radical, wherein said aryl radical is optionally substituted;
R'1 and R'2 represent an arylene, alkylene or cycloalkylene radical, wherein said radicals being optionally substituted; and
R3 and R4 represent independently a hydrogen atom, methyl radical, or an alkyl radical.

2. The method according to claim 1, wherein the (co)polymerization is of dilactones.

3. The method according to claim 1, wherein the (co)polymerization is of lactide and/or glycolide.

4. The method according to claim 3, wherein the (co)polymerization is of lactide.

5. The method according to claim 1, wherein said base is a tertiary amine.

6. The method according to claim 1, wherein said base is diisopropylethylamine; sparteine; N,N-dimethylcyclohexylamine; N,N,N"N"-tetramethyl-1,2-cyclohexanediamine; or 4-dimethylaminopyridine.

7. The method according to claim 1, wherein R1 and R2 represent independently a phenyl, alkyl or haloalkyl radical in the monosulphonamide of formula (I).

8. The method according to claim 1, wherein the monosulphonamide of formula (I) is:

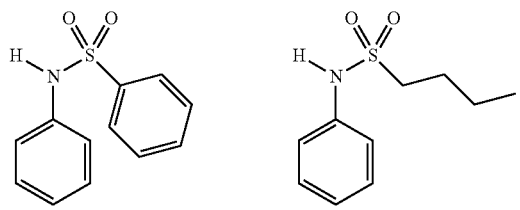

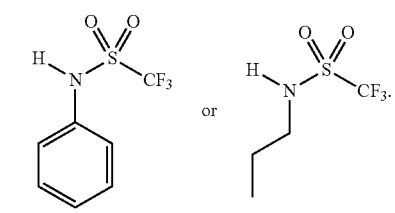

or

9. The method according to claim 1, wherein R3 and R4 represent independently a hydrogen atom or a methyl radical in the bisulphonamide of formula (IIa) or (IIb).

10. The method according to claim 1, wherein R3 and R4 represent a hydrogen atom in the bisulphonamide of formula (IIa) or (IIb).

11. The method according to claim 1, wherein R1 and R2 represent an optionally substituted phenyl radical, alkyl or haloalkyl; R'1 represents a cycloalkylene, alkylene radical optionally substituted by a phenyl radical; and R'2 represents an alkylene or phenylene radical in the bisulphonamide of formula (IIa) or (IIb).

12. The method according to claim 1, wherein R1 and R2 represent an alkyl, trifluoromethyl or phenyl radical optionally substituted by methyl or trifluoromethyl in the bisulphonamide of formula (IIa) or (IIb).

13. The method according to claim 1, wherein the the bisulphonamide of formula (IIa) or (IIb) is:

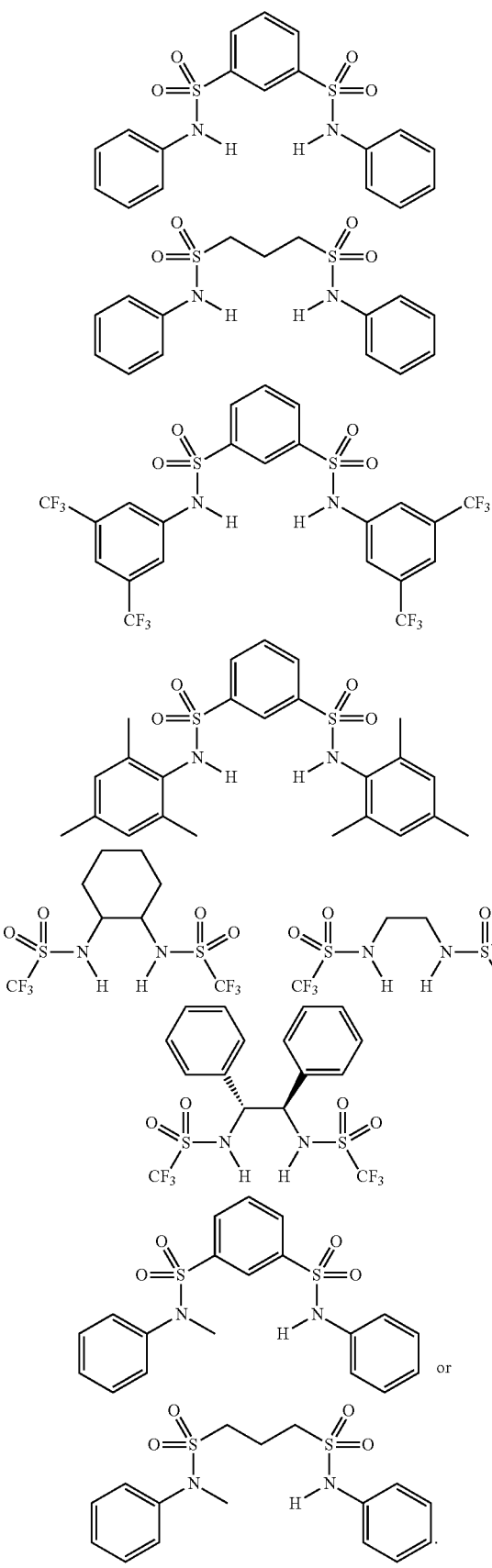
or
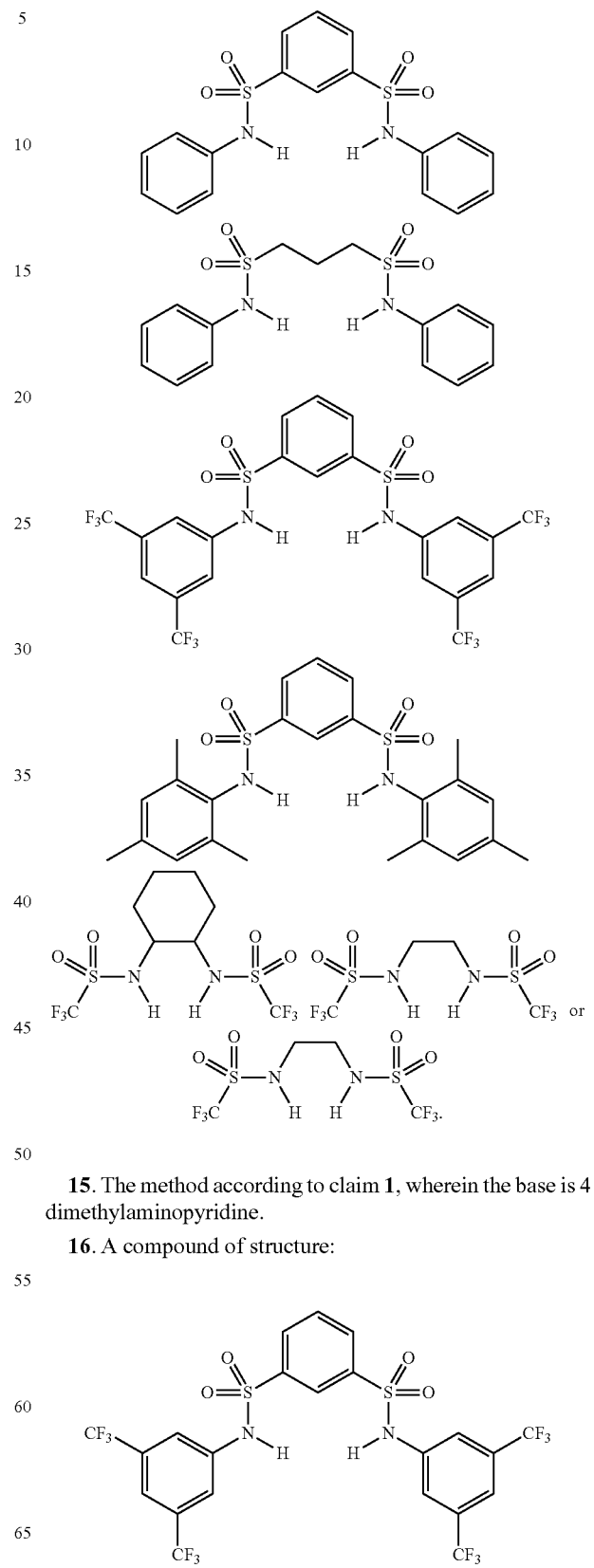
14. The method according to claim 1, wherein the the bisulphonamide of formula (IIa) or (IIb) is:
15. The method according to claim 1, wherein the base is 4 dimethylaminopyridine.
16. A compound of structure:

-continued

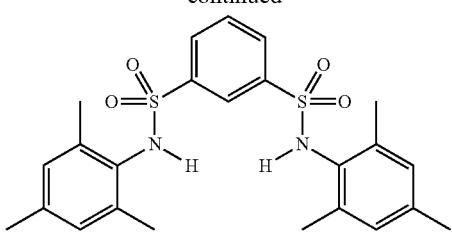

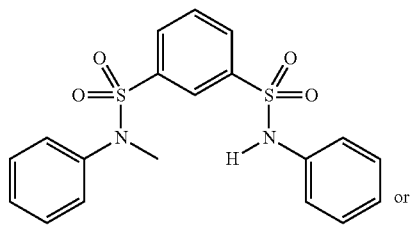 or

-continued

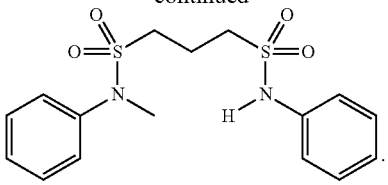

17. The method according to claim 1, wherein said method is performed in the presence of a solvent at a temperature between 0° C. and 250° C., for a duration of a few minutes to 300 hours.

18. The method according to claim 17, wherein said solvent is at a temperature between ambient temperature and 150° C., for a duration of one hour to 72 hours.

19. The method according to claim 1, wherein, the lactone(s) is monomeric lactide and/or glycolide.

20. The method according to claim 9, wherein R3 and R4 represent a hydrogen atom.

* * * * *